_United States Patent_ [19]

Noszticzius et al.

[11] 4,201,550

[45] May 6, 1980

[54] PROCESS AND APPARATUS FOR THE DETERMINATION OF THE TOTAL ORGANIC SUBSTANCE CONTENT OF GASES BY A FLAME IONIZATION DETECTOR

[76] Inventors: Zoltán Noszticzius, Karinthy Frigyes ut 18/b, 1111 Budapest; Gábor Patonay, Váli utca 4, 1117 Budapest; György Pálmai, Biró utca 17/b, 1122 Budapest; Károly Oláh, Vörösvari ut 39, 1035 Budapest; Gyula Gáspár, Gábor Áron utca 29, 1026 Budapest; György Székely, György Aladár utca 8, 1125 Budapest; Zsófia Vajta, Fenyö utca 8, 1016 Budapest; Károly Langer, Möricz Zsigmond utca 25, 2000 Szentendre; Ferenc Szommer, Böszörmenyi ut 34/b, 1126 Budapest, all of Hungary

[21] Appl. No.: 861,968

[22] Filed: Dec. 19, 1977

[30] Foreign Application Priority Data

Dec. 23, 1976 [HU] Hungary .............................. CE 1114

[51] Int. Cl.² ...................... G01N 27/62; B01D 13/00
[52] U.S. Cl. ...................................... 23/232 E; 55/16;
55/158; 422/54; 422/94; 422/98; 422/101
[58] Field of Search ............. 23/237 E, 254 E, 255 E,
23/254 EF; 55/16, 158; 422/54, 94, 98, 101

[56] References Cited

U.S. PATENT DOCUMENTS

| 2,991,158 | 7/1961 | Harley .............................. 23/254 EF |
| 3,398,505 | 8/1968 | Llewellyn ............................... 55/16 |
| 3,502,439 | 3/1970 | Reece et al. ..................... 23/254 EF |
| 3,545,931 | 12/1970 | McKinley, Jr. .................... 23/254 E |
| 3,674,435 | 7/1972 | Van Luik, Jr. et al. ............. 55/16 X |
| 3,926,561 | 12/1975 | Lucero .................................. 55/16 X |

FOREIGN PATENT DOCUMENTS 1446637  8/1976  United Kingdom .

_Primary Examiner_—Joseph Scovronek

[57] ABSTRACT

Process and apparatus for the determination of the total organic substance content of gases by a flame ionization detector, respectively comprising the steps and means for allowing components of the gas to be analyzed to diffuse through a pore-free polymeric membrane having a permeability coefficient that exceeds $10^{-7}$ Ncm³.cm/sec.cm².Hgcm. related to the total organic substance contained in the gas, leading the gas components into a flame of another gas that contains hydrogen, passing the burning hydrogen-containing gas along one side of the membrane at a flow rate of max. 25 cm³/min., simultaneously pumping the gas to be analyzed on the other side of the membrane at a volumetric flow of at least tenfold of that of the other gas, diffusing the organic substances to be determined through the membrane, subsequently leading the organic substances that have diffused through the membrane, in admixture with the other gas, into the flame ionization detector, and determining the total organic substances therein.

6 Claims, 4 Drawing Figures

U.S. Patent
May 6, 1980
4,201,550
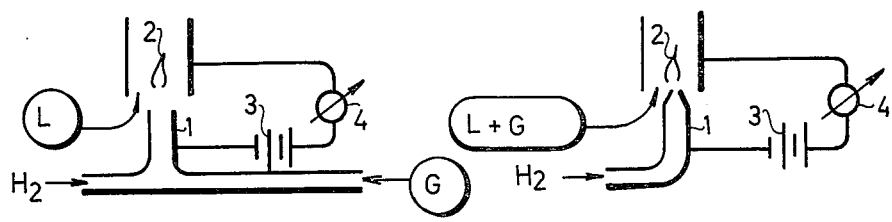
Fig.1a
PRIOR ART
Fig.1b
PRIOR ART
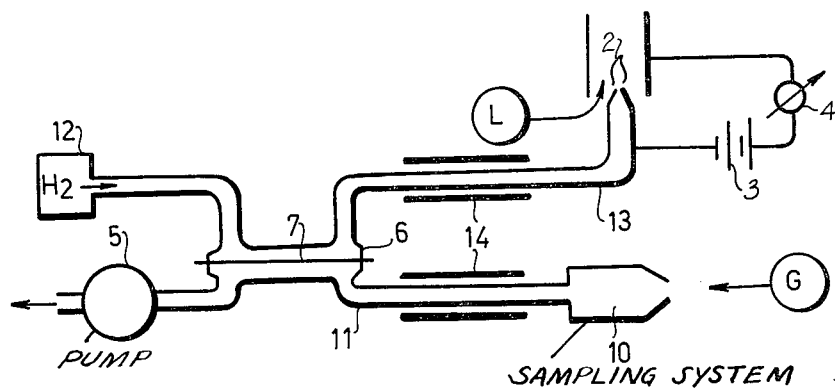
Fig.2
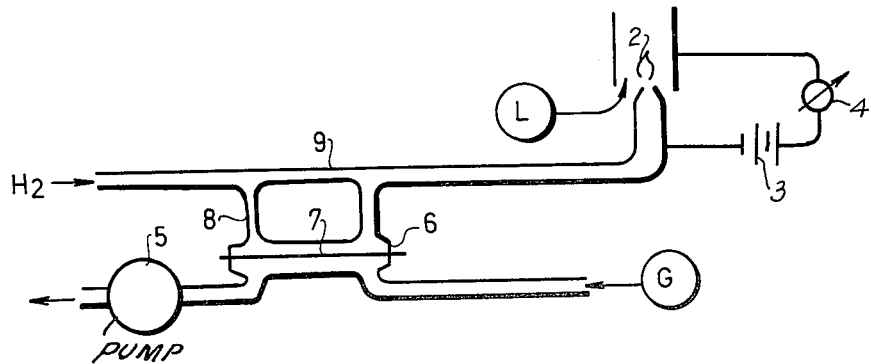
Fig.3

PROCESS AND APPARATUS FOR THE DETERMINATION OF THE TOTAL ORGANIC SUBSTANCE CONTENT OF GASES BY A FLAME IONIZATION DETECTOR

The present invention relates to a process and an apparatus for the determination of the total organic substance content of gases by a flame ionization detector.

It is well-known that for the continuous quantitative analysis of organic substances (most frequently hydrocarbons) in various gases (first of all air) instruments based on infrared absorption and flame ionization detectors are the most widely used (Patterson D. J., Henein N. A.: Emissions from Combustion Engines and Their Control, Ann Arbor Science Publ. Inc., Ann Arbor, 1972. p. 305).

Both methods are generally used for the determination of the total organic substance content of gases. The simultaneous quantitative determination of the individual components is rather difficult and can be effected by gas chromatography only in the simplest cases. On the other hand, separation of the individual compounds is often unnecessary. For instance the operation of a combustion engine can sufficiently be characterized by the total amount of the unburnt hydrocarbons exhausted, consequently it is sufficient if the totality thereof is determined and the quantity of such hydrocarbons is expressed in an equivalent concentration of methane or n-hexane.

When using non-dispersive infrared (NDIR) analyzers not only the interference from carbon dioxide, carbon monoxide and especially steam has a disturbing effect, but the change in the molar ratios of the hydrocarbons also has an influence on the measured values. The sensitivity is not proportional to the number of the carbon atoms; the infrared instruments are, therefore, more and more superseded by the flame ionization detectors (FIDs).

Although the sensitivity of these detectors surpasses that of the infrared methods by several orders of magnitude, they cannot be used for the determination of concentrations exceeding one to two percent by volume, while the non-dispersive infrared methods work over the entire concentration range of 0 to 100% by volume.

Another drawback of the flame ionization detectors is the fact that they are sensitive to fluctuations in the flow rate of the gas sample.

A measuring set-up that is relatively insensitive to the changes in the flow rate of the gas sample is obtained if the components to be determined are led into the detector by diffusion through a membrane. British Pat. No. 1,446,637 describes a method where the test gas is passed along one side of a membrane that is permeable with respect to the component to be tested, in an infrared, colorimetric etc. analyzer, while the carrier gas is passed at a constant volumetric flow along the other side of the membrane. This experimental set-up avoids the entry of steam, solid particles and other undesirable components into the detector.

On the other hand, proper choice of membrane ensures that only the component reaches the carrier gas of which the determination is intended. If the cell containing the membrane is kept at a constant temperature the concentration of the component to be determined in the carrier gas can be kept proportional to its concentration in the test gas.

In other words, the operation of this apparatus is based on dilution, which means for example that the $SO_2$ content of waste gases is allowed to mix with a pure air flow, in a manner ensuring that the concentration thereof in the carrier gas is proportional to its concentration in the waste gas.

This method, however, cannot be used for the determination of organic substances by flame ionization detection since it is not suitable for the determination of the total quantity of organic substances in the gas sample, proportional to the number of carbon atoms in their molecules. Another disadvantage of this method is that its operation is stable only if the permeability of the membrane is constant, i.e. any factor resulting in a change of the permeability has a disturbing effect. The use of a thermostat for the membrane is therefore unavoidable, and if the membrane becomes contaminated or if ageing occurs, the membrane has to be replaced. In this case the system naturally has to be recalibrated.

Another drawback of this method is that the permeability of the membrane employed is different for various organic substances. If a simultaneous determination of more components is intended, this means that the proportionality factor will be different for the various components, although the quantities of the tested components in the carrier gas are proportional to their quantities in the gas to be analysed. This invention relates to a novel method that combines the advantages of the infrared and the flame ionization methods, which is thus suitable for the determination of organic materials in gases in the total concentration range of 0 to 100% by volume with a high sensitivity.

Consequently, there is disclosed a method for the determination of the total organic substance content of various gases by flame ionization detectors, which ensures that the proportion of the various organic substances in the fuel (burning) gas is identical with their original proportion in the gas sample being analyzed, and that the signal obtained in the detector is independent of the fluctuation of the flow rate of the sample, within the accuracy of the measurement.

The object of the invention is also to provide an apparatus in which partial pressures in two sections of a cell, divided by a membrane, can easily be equalized during the measurement.

According to the invention the above objects are accomplished in that the fuel gas is passed along one side of the membrane at a rate of at most 25 cm$^3$/min., while the gas to be analysed is pumped along the other side of the membrane at a volumetric flow at least ten times as high as that of the burning gas. The organic substances to be detected are diffused through the membrane, which is pore-free, polymeric and has a permeability coefficient above $10^{-7}$ Ncm$^3$.cm/sec.cm$^2$.Hgcm related to all the organic substances. The organic substances diffused through the membrane are subsequently led into the flame ionization detector, admixed with the fuel gas, and then detected in a manner known per se.

According to a preferred feature of the method according to the invention at most one tenth of the burning gas reaching the flame ionization detector is passed along the one side of the membrane, it is then combined with the rest of the fuel gas together with the organic substances diffused through the membrane and led into the detector.

The fuel gas is preferably passed along the membrane at a constant flow rate.

The apparatus according to this invention is equipped with a hydrogen-containing fuel (burning) gas or hydrogen source, for example with an electrolytic cell that generates hydrogen, with a gas sampling system, a pump transmitting the gas to be analysed, and a flame ionization detector. The latter includes a diffusion chamber divided into two sections by a membrane, one section being connected with the gas sampling system, and the other with the gas source and the flame ionization detector. The permeability coefficient of the membrane is preferably above $10^{-7}$ Ncm$^3$.cm/sec.cm$^2$.Hgcm for all the organic substances tested as mentioned before.

The sampling system, the diffusion chamber of the instrument as well as the pipe lines connecting the flame ionization detector to the diffusion chamber are preferably equipped with heaters.

The invention is based upon the recognition that if the organic component(s) of the gas sample is (are) diffused into the hydrogen burnt in the detector through a membrane, signals proportional to the partial pressures of the organic compounds present are obtained. The partial pressures measured on both sides of the membranes can be made substantially equal when the membrane and the flow rates are suitably chosen.

Further details of the invention are to be illustrated by the attached figures, wherein FIG. 1a is a sketch of a conventional flame ionization detector;

FIG. 1b is another set-up of a conventional flame ionization apparatus;

FIG. 2 shows an exemplary apparatus according to the invention; and

FIG. 3 shows another embodiment of the apparatus according to the invention.

In the flame ionization detector shown in FIGS. 1a and 1b hydrogen or hydrogen-containing fuel (burning) gas, effusing through a nozzle 1 (e.g. hydrogen/nitrogen or hydrogen/helium mixture identified as a matter of example as H$_2$) is burnt in air L and a flame 2 is placed between electrodes (one suitably being the nozzle itself). From a source 3 of a direct voltage of 100 to 200 V is connected to between the electrodes, and the intensity of the current in the circuit is measured by an ammeter 4. In case of pure hydrogen and air the intensity of the current can be less than 1 pA (picoampere). The hydrogen is obtained from a gas cylinder or generated from water by electrolysis. The purity of the air is less critical, in general atmospheric air is suitable. If organic compounds get to the flame 2 the intensity of the current increases due to the ionization (sensitivity: some pA/ppm organic material). Inorganic gases cause no ionization.

In practice, two conventional constructions are known. In the construction according to FIG. 1a a gas G to be analysed is admixed with the hydrogen H$_2$ and the gas mixture is burnt in the air L.

The construction illustrated in FIG. 1b differs from the set-up shown on FIG. 1a in that there the hydrogen or the hydrogen-containing fuel (burning) gas is admixed with the gas G to be analysed not in the pipe line but the gas is led to the flame 2 together with the air L (L+G). The latter construction is simpler but has several drawbacks.

Since the oxygen, unavoidable for the burning, has to be secured from the oxygen content of the gas to be analysed the direct analysis of samples is impossible that do not contain any or only some oxygen. A further drawback of this construction is that the sensitivity, similarly to that of the infrared gas analyzers, is not proportional to the number of the carbon atoms. This requirement is only met by the construction of FIG. 1a.

This can be clearly seen from the following table where the sensitivities obtained during the measurements carried out by infrared and both flame ionisation methods on various hydrocarbons are illustrated. The sensitivities are related to one carbon atom, taking n-hexane as 100 (Chapman R. L.: Environmental Pollution Instrumentation /Selected paper from a Symp./ Pittsburg, /1969/, p. 18. and Hiborn J.: Journal of Air Pollution Control Assoc. 24 /1974/ 983).

|  | NDIR | FID Figure 1a | FID Figure 1b |
|---|---|---|---|
| methane | 30 | 104 | 450 |
| propane | 103 | 103 | 120 |
| n-hexane | 100 | 100 | 100 |
| benzene | 2 | 105 | 300 |

It should be noted that with the construction 1a the obtained signal is proportional to the number of the carbon atoms within 5%, while with the other two methods considerable discrepancies can be observed. The organic substance content of a gas containing several kinds of organic compounds can be determined exclusively by a flame ionization detector having the construction of FIG. 1a. At the same time, the disadvantage of the flame ionization detectors compared to the NDIR method is that the obtained signal (current density) is the function of the gas flow rate which should, therefore, be stabilized. Moreover, the sample passes through a pump before reaching the detector, which usually results in a change in the composition of the gas.

In FIG. 2 the set-up according to the invention is shown. The gas to be analysed is pumped through a sampling system 10 and a pipe line 11 by a pump 5 into one section of a diffusion chamber 6 divided into two sections by a membrane 7. Meanwhile hydrogen generated from a source 12 is passed along the other side of the membrane in a reverse current. Parts 8, 9 will be described somewhat later. The hydrogen source 12, preferably fashioned as an electrolytic cell, is suitably supplied from an electric current generator which ensures the electronic stabilization of the hydrogen flow.

The organic compounds diffusing from the gas G to be analysed through the membrane 7 reach the flame ionization detector (not shown but provided in all illustrations above the nozzle 1 and the flame 2 in a known manner) together with the hydrogen through the pipe line 13. In the detector the hydrogen H$_2$ is burnt with the air L pumped towards the detector.

If desired, the air can be purified by passing the same through a filter filled with active carbon or some other adsorbent.

If the analysis of gases is intended that contain organic substances which condense easily (e.g. unburnt hydrocarbons present in the exhaust gases of Diesel motors), the pipe lines 11, 13 connecting the sampling system 10 with the diffusion chamber 6, and the latter with the flame ionization detector, respectively, can be heated with heaters 14.

In the cell or chamber 6 the material balance for the organic substances is as follows:

Organic substance input (carried by the gas sample) = Organic substance output (carried by the gas sample + hydrogen), i.e.

$$J_g \cdot p_g^b = J_g \cdot p_g^a + J_H \cdot p_H \qquad (1)$$

where $J_g$ and $J_H$ stand for the volumetric flow of the gas sample and of the hydrogen, respectively (cm³/sec.) and $p_H, p_g^b$ and $p_g^a$ represent the partial pressures of the organic substance in the hydrogen, as well as in the gas sample before and after the membrane (Hgcm).

If the membrane is pore-free, i.e. the organic substance can pass through the membrane only by diffusion in the stationary state the organic substance flow that leaves together with the hydrogen is equal to the organic substance flow that diffuses through the membrane, which is proportional to the difference between the partial pressures measured on the two sides of the membrane:

$$J_H \cdot p_H = K(p_g^a - p_H) \qquad (2)$$

where $K = kRT$ (R is the gas constant and T is the absolute temperature.

On the basis of the equations (1) and (2) the partial pressure of an organic substance on the hydrogen side can be expressed as a function of its partial pressure measured in the gas sample:

$$p_H = \frac{p_g^b}{1 + \frac{J_H}{J_g} + \frac{J_H}{kRT}} \qquad (3)$$

in which $k = (A \cdot P)/l$, wherein

A represents the surface of the membrane (cm²), l is the thickness of the membrane (cm), P stands for the so-called permeability coefficient characteristic of the organic substance pair (N.cm³.cm/sec.cm².Hgcm), which shows how much Ncm³ of an organic substance diffuses through a membrane having a surface of 1 cm² and a thickness of 1 cm, under 1 Hgcm of partial pressure difference.

From the equation (3) it can be seen that at a given temperature and volumetric hydrogen flow, the partial pressure of an organic substance on the hydrogen side depends on the flow velocity of the gas sample and on the permeability coefficient of the membrane.

If the membrane has a high permeability related to all the organic substances contained in the gas sample ($J_H/KRT << 1$) and if the volumetric velocity of the gas sample is more than 10-fold of that of the hydrogen, —i.e. $J_H/J_g < 0.1$—the partial pressure of the organic substances on the hydrogen side is more than 90% of their partial pressure in the gas sample; consequently, the partial pressures on the two sides of the membrane are approximately or almost identical ($p_H \approx p_g^b$).

In order to obtain approximately equal partial pressures on the two sides of the membrane, i.e. to provide a semi-equilibrium situation, it should be ensured that the flow rate of the burning gas is not too high. The burning gas is, therefore, passed according to the invention along the membrane at a rate of at most 25 cm³/min. This limitation of the flow rate of the burning gas makes it possible, on the other hand, that a suitable signal-to-noise proportion is obtained, since it has a disadvantageous effect on the flame ionization detectors if hydrogen is present at a too high concentration.

In this case, the proportions of the various hydrocarbons in the hydrogen are the same as their original proportions in the gas sample. This variant is, therefore, especially suitable for the determination of the total quantity of a large variety of hydrocarbons contained in various gases, in a total concentration less than 1% by volume (for instance for the analysis of the emissions from combustion engines).

As a membrane, for instance, silicone rubber of a thickness of 1 to 2 μm can be used.

The main advantages of the above-outlined method are as follows:

(a) Its sensitivity is better than that of the method according to the construction of FIG. 1a since, in case of identical organic substance concentrations on the gas side, more organic substances get here into the flame, the partial pressures of the organic substances on the hydrogen and the gas sides being practically identical.

(b) By using a pump for the transmission of the gas a contamination of the sample is prevented before reaching the detector; no change takes place in the composition of the gas sample prior to detection.

(c) If the volumetric flow of the gas sample exceeds a limit value, this method is insensitive to changes in the flow velocity of the sample.

(d) The method is insensitive to changes of the sample temperature within a wide range.

(e) This method is also insensitive to other factors having an influence on the permeability of the membrane (e.g. ageing, contamination, replacement of the membrane, etc.) when the condition $J_H/kRT << 1$ is fulfilled.

The equality of the partial pressures of the two sides of the membrane can be ensured also in case of higher organic substance concentrations, as shown in FIG. 3 where only a small part of the hydrogen flow is led into the cell 6 through a choke or restrictor line 8; the remaining part passes through a choke or restrictor line 9, and the two flows are led into the detector together, after being combined. By a suitable choice of the flow resistances of the lines 8, 9 it is ensured that less than 1/10 of the total hydrogen flow gets into the cell 6.

If, for example, the total volumetric flow of the hydrogen is 25 cm³/min., and from this 2.5 cm³/min. pass through the diffusion cell, the equation $p_H = p_g/10$ will be true for all the components in the main line. This provides a signal proportional to the number of the carbon atoms even for tenfold organic substance concentrations in the gas to be analysed. If the volumetric flow of the gas sample is at least 250 cm³/min. it need not be stabilized since the error due to its fluctuation is less than 1%.

From the equation (3) is can also be seen that a small hydrogen flow $J_H$ along the membrane is favourable for the equalization of the partial pressures on the two sides of the membrane, since in this case the members beside the above-named volumetric hydrogen-flow unit in the denominator of the fraction in equation 3 can be neglected.

On the other hand, it is advisable to stabilize the hydrogen flow since the quantity of the organic substances reaching the detector per time unit, and consequently also the obtained signal, is (are) proportional to the volumetric hydrogen flow. This can easily be accomplished if the hydrogen is generated by electrolysis where electronic stabilization of the electrolytic current avoids fluctuations in the volumetric flow of the hydrogen.

By a suitable choice of the sizes of the cell employed and the pipe line connecting the cell with the detector it can be ensured that the changes in the composition of the gas are followed within a very short time corresponding changes in the obtained signal. If the cell volumes of the two sides of the membrane are less than 1 cm$^3$, a response time shorter than 1 sec. can be achieved.

The area of the membrane is generally 1 to 10 cm$^2$. For supporting the thin membrane, generally known methods can be used. In order to improve organic material transfer, the hydrogen and the gas sample are preferably led in counterflow.

What we claim is:

1. A process for the determination of the total content of organic substances in a gas to be analyzed by the flame ionization method, comprising the steps of: allowing the components of the gas to diffuse through a pore-free polymeric membrane having a permeability coefficient that exceeds $10^{-7}$ Ncm$^3$.cm/sec.cm$^2$.Hgcm. related to the total organic substance contained in the gas; igniting another gas that contains hydrogen; leading components of the gas being analyzed into the flame of the other gas; passing the other gas along one side of the membrane at a flow rate of maximum 25 cm$^3$/min.; simultaneously pumping the gas being analyzed on the other side of the membrane at a volumetric flow of at least tenfold of that of the other gas; wherein the partial pressures of the gas being analyzed and of the other gas are nearly the same; diffusing the organic substances to be determined through the membrane; subsequently leading the organic substances that have diffused through the membrane, in admixture with the other gas, into an ionization detector that incorporates the flame; and determining the total organic substances therein.

2. The process as defined in claim 1, wherein maximum 1/10 part of the other gas led into the flame ionization detector is passed along the one membrane side, which gas part is then combined with the rest of the other gas, together with the organic substances diffused through the membrane and led into the detector.

3. The process as defined in claim 1, wherein the other gas is passed along the membrane at a constant flow rate.

4. An apparatus for the determination of the total content of organic substances in a gas to be analyzed by the flame ionization method, comprising: a source of another, hydrogen-containing gas; a sampling system for the gas being analyzed; a pump for transmission of the latter gas; and a flame ionization detector including a diffusion chamber divided into two sections by a membrane; one of said sections being connected to said sampling system; wherein said membrane is a pore-free polymeric membrane having a permeability coefficient that exceeds $10^{-7}$ Ncm$^3$.cm/sec.cm$^2$.Hgcm. related to the total organic substance contained in the gas being analyzed; the other of said sections of the chamber is connected to said other gas source as well as to said detector; and pipe lines that connect said sampling system as well as said flame ionization detector with said chamber; wherein the partial pressures of the gas being analyzed and of said other gas are nearly the same.

5. The apparatus as defined in claim 4, further comprising at least one heater for at least one of said pipe lines.

6. The apparatus as defined in claim 4, wherein said other gas source is constituted by an electrolytic cell that produces hydrogen.

* * * * *